US012629125B2

(12) United States Patent
Liu

(10) Patent No.: US 12,629,125 B2
(45) Date of Patent: May 19, 2026

(54) SCATTERING EVENT SCREENING METHOD AND DEVICE, AND PET SYSTEM, ELECTRONIC APPARATUS AND STORAGE MEDIUM

(71) Applicant: WUHAN UNITED IMAGING LIFE SCIENCE INSTRUMENT CO., LTD., Wuhan (CN)

(72) Inventor: Longpeng Liu, Wuhan (CN)

(73) Assignee: WUHAN UNITED IMAGING LIFE SCIENCE INSTRUMENT CO., LTD., Wuhan (CN)

( * ) Notice: Subject to any disclaimer, the term of this patent is extended or adjusted under 35 U.S.C. 154(b) by 195 days.

(21) Appl. No.: 18/710,205

(22) PCT Filed: Dec. 8, 2021

(86) PCT No.: PCT/CN2021/136588
§ 371 (c)(1),
(2) Date: May 15, 2024

(87) PCT Pub. No.: WO2023/087433
PCT Pub. Date: May 25, 2023

(65) Prior Publication Data
US 2025/0352161 A1 Nov. 20, 2025

(30) Foreign Application Priority Data

Nov. 16, 2021 (CN) .......................... 202111354919.7

(51) Int. Cl.
*A61B 6/03* (2006.01)
*A61B 6/00* (2024.01)
(Continued)

(52) U.S. Cl.
CPC ............ *A61B 6/5282* (2013.01); *A61B 6/037* (2013.01); *A61B 6/4208* (2013.01); *G01T 1/2985* (2013.01)

(58) Field of Classification Search
CPC ..... A61B 6/5282; A61B 6/037; A61B 6/4208; G01T 1/2985
See application file for complete search history.

(56) References Cited

U.S. PATENT DOCUMENTS 11,257,260 B2 * 2/2022 Wilk ...................... A61B 6/483
12,004,887 B2 * 6/2024 Kawata ................ A61B 6/4258
(Continued)

FOREIGN PATENT DOCUMENTS

CN 109091158 A 12/2018
CN 109875592 A 6/2019
(Continued)

OTHER PUBLICATIONS

International Search Report in PCT/CN2021/136588 mailed on Aug. 17, 2022, 7 pages.
(Continued)

*Primary Examiner* — David J Makiya
(74) *Attorney, Agent, or Firm* — METIS IP LLC

(57) ABSTRACT

The embodiments of the present disclosure provide a method and device for screening scattering events, a PET system, an electronic device, and a storage medium. The method includes obtaining an absorption depth curve of photons of a detector of the PET system, dividing the detector into a first region and a second region along a depth direction of the detector based on the absorption depth curve; determining a first energy window in the first region to screen scattering events occurred in the scanning target; and determining a plurality of second energy windows in the second region to retain scattering events occurred in the
(Continued)

Obtaining an absorption depth curve of photons of a detector of the PET system, dividing the detector into a first region and a second region along a depth direction of the detector based on the absorption depth curve — 310

Determining a first energy window in the first region to screen scattering events occurred in the scanning target — 320

Determining a plurality of second energy windows in the second region to retain scattering events occurred in the detector, wherein the plurality of second energy windows are sequentially widened in the depth direction — 330 detector. The detector includes a plurality of detector layers, the depth direction of the detector is a direction of the plurality of detector layers away from a scanning target, and the plurality of second energy windows are sequentially widened in the depth direction.

20 Claims, 8 Drawing Sheets

(51) Int. Cl.
  *A61B 6/42*        (2024.01)
  *G01T 1/29*        (2006.01)

(56)                  References Cited

U.S. PATENT DOCUMENTS

| | | | |
|---|---|---|---|
| 12,449,554 | B2 * | 10/2025 | Braeuninger-Weimer ................. G01T 1/20185 |
| 2010/0032574 | A1 | 2/2010 | Yoshida et al. |
| 2011/0174980 | A1 | 7/2011 | Gagnon |
| 2015/0289825 | A1 | 10/2015 | Lage et al. |
| 2017/0212251 | A1 | 7/2017 | Hadjioannou et al. |
| 2019/0212457 | A1 | 7/2019 | Li et al. |
| 2019/0353807 | A1 * | 11/2019 | Furenlid ............. G01T 1/20185 |
| 2020/0151918 | A1 | 5/2020 | Watson et al. |

FOREIGN PATENT DOCUMENTS

| | | |
|---|---|---|
| CN | 111505699 A | 8/2020 |
| JP | 2011153975 A | 8/2011 |

OTHER PUBLICATIONS

Written Opinion in PCT/CN2021/136588 mailed on Aug. 17, 2022, 5 pages.

Lee, Minsun et al., Novel inter-crystal scattering event identification method for PET detectors, Physics in Medicine & Biology, 13 pages, 2018.

Zhang, Chunhui et al., The effects of inter-crystal scattering events on the performance of PET detectors, Physics in Medicine and Biology, 10 pages, 2019.

* cited by examiner

101

102

103

104

Reconstruction
Machine

True
Conforming
Events

Random
Conforming
Events

Scattering
Conforming Events
Occurred In A
scanning target

Scattering
Conforming
Events Occurred
In A Detector

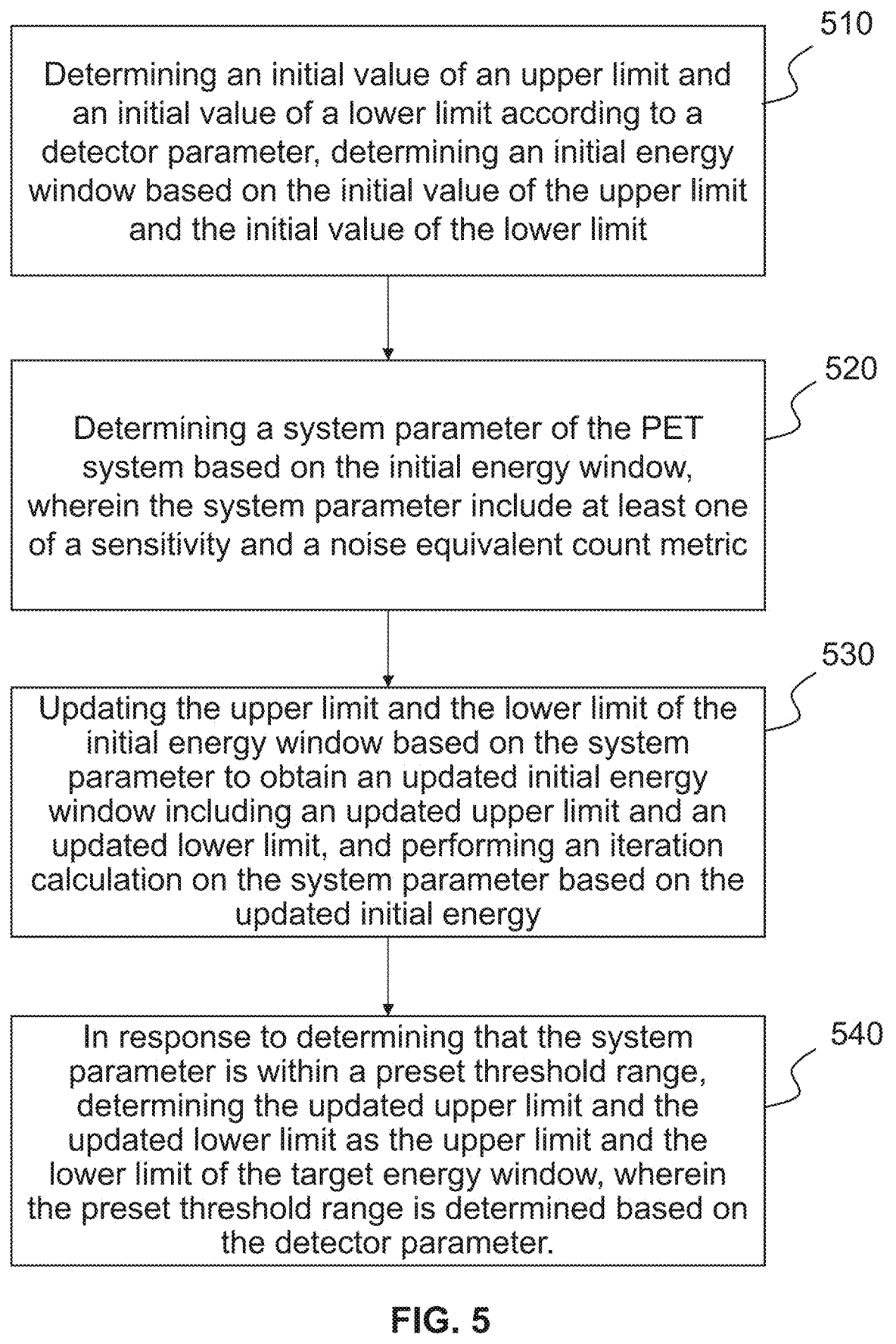

510

Determining an initial value of an upper limit and an initial value of a lower limit according to a detector parameter, determining an initial energy window based on the initial value of the upper limit and the initial value of the lower limit

520

Determining a system parameter of the PET system based on the initial energy window, wherein the system parameter include at least one of a sensitivity and a noise equivalent count metric

530

Updating the upper limit and the lower limit of the initial energy window based on the system parameter to obtain an updated initial energy window including an updated upper limit and an updated lower limit, and performing an iteration calculation on the system parameter based on the updated initial energy

540

In response to determining that the system parameter is within a preset threshold range, determining the updated upper limit and the updated lower limit as the upper limit and the lower limit of the target energy window, wherein the preset threshold range is determined based on the detector parameter.

FIG. 5

Figure 6:
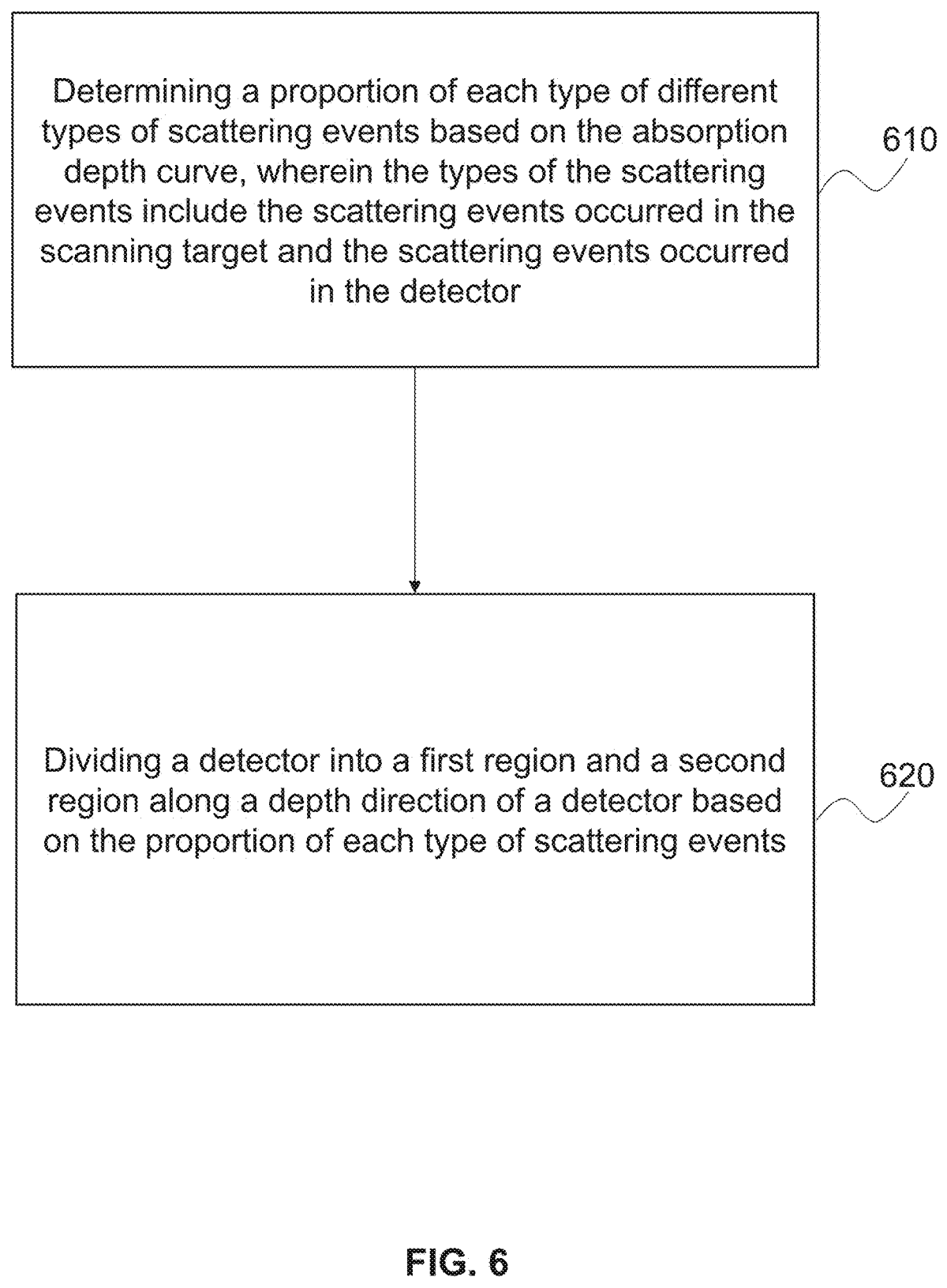

Determining a proportion of each type of different types of scattering events based on the absorption depth curve, wherein the types of the scattering events include the scattering events occurred in the scanning target and the scattering events occurred in the detector

610

Dividing a detector into a first region and a second region along a depth direction of a detector based on the proportion of each type of scattering events

SCATTERING EVENT SCREENING METHOD AND DEVICE, AND PET SYSTEM, ELECTRONIC APPARATUS AND STORAGE MEDIUM

CROSS-REFERENCE TO RELATED APPLICATIONS

This application is a U.S. national stage under 35 U.S.C. § 371 of International Application No. PCT/CN2021/136588, filed on Dec. 8, 2021, which claims priority to Chinese patent application No. 202111354919.7, field on Nov. 16, 2021, entitled "Scattering Event Screening Method and Device, And PET System, Electronic Apparatus And Storage Medium", the entire contents of each of which are incorporated herein by reference.

TECHNICAL FIELD

The present disclosure relates to the technical field of radionuclide imaging, and in particular to methods, devices for screening scattering events, pet systems, electronic devices, and storage mediums.

BACKGROUND

Positron Emission Computed Tomography (PET) is an advanced clinical or preclinical radionuclide imaging technique in the technical field of nuclear medicine. Before scanning an object by a PET system, the object needs to be injected with a tracer containing radionuclides, which decays and produces positrons in the object, and the positrons meet with the electrons in the object to generate a pair of γ photons with the same energy in opposite directions, the pair of γ-photons pass through the tissues of the object and be received by a detector of the PET system, the imaging data is obtained based on the results. The scattering of the γ photons in the field of view of the PET system conforms to the events, which causes an error in the positioning of the line of response (LOR) in the PET system, thereby reducing a signal-to-noise ratio of the data, worsening the quality of the PET reconstructed image.

In the related technology, the PET system screens scattering coincidence events by using an "energy window". In reality, the scattering process occurs both in a scanning object and in a scintillation crystal of the detector. Only the scattering coincidence events in the scanning object cause the error of the position of the LOR, the scattering coincidence events are unable to affect the LOR. The method of determining the energy window in the related technology cannot distinguish between two types of scattering coincidence events, causing the sensitivity of the PET system to be relatively low.

Currently, there is no effective solution to address the problem that the method for determining the energy window in the related technology is unable to distinguish between the two scattering coincidence events such and thereby causing the sensitivity of the PET system to be relatively low.

SUMMARY

According to the embodiments of the present disclosure, a method and device for screening scattering events, a PET system, an electronic device, and a storage medium are provided to at least address the problem in the related art that the method for determining the energy window in the related technology may be unable to distinguish between the two types of scattering compliant events and thereby causing the sensitivity of the PET system to be relatively low.

According to the embodiments of the present disclosure, a method for screening scattering events is provided, the method may be applied to a PET system. The method includes obtaining an absorption depth curve of photons of a detector of the PET system, dividing the detector into a first region and a second region along a depth direction of the detector based on the absorption depth curve; determining a first energy window in the first region to screen scattering events occurred in the scanning target; and determine a plurality of second energy windows in the second region to retain scattering events occurred in the detector. The detector may include a plurality of detector layers, and the depth direction of the detector may be a direction of the plurality of detector layers away from a scanning target. The plurality of second energy windows may be sequentially widened in the depth direction.

In some embodiments, an upper limit and a lower limit of a target energy window may be obtained based on a detector parameter of the detector. The target energy window may include a first energy window and/or a second energy window, and the detector parameter may include at least one of: an energy resolution of the detector in the plurality of detector layers, a material type of a scintillation crystal in the detector, a size of the scintillation crystal, or a resolution of a depth of interaction of the photons in the PET system.

In some embodiments, the obtaining the upper limit and the lower limit of the target energy window based on the detector parameter of the detector may include: determining an initial value of the upper limit and an initial value of the lower limit according to the detector parameter, determining an initial energy window based on the initial value of the upper limit and the initial value of the lower limit; determining the system parameter of the PET system based on the initial energy window; updating the upper limit and the lower limit of the initial energy window based on the system parameter to obtain an updated initial energy window including an updated upper limit and an updated lower limit, performing an iteration calculation on the system parameter based on the updated initial energy window; and in response to determining that the system parameter is in a preset threshold range, determining the updated upper limit and the updated lower limit as the upper limit and the lower limit of the target energy window. The system parameter may include at least one of a sensitivity and a noise equivalent count metric, and the preset threshold range is determined based on the detector parameter.

In some embodiments, the obtaining the absorption depth curve of the photons of the detector of the PET system, and dividing the detector into the first region and the second region along the depth direction of the detector based on the absorption depth curve may include: determining a proportion of each type of a plurality of types of scattering events based on the absorption depth curve; and dividing the detector into the first region and the second region along the depth direction of the detector based on the proportion of the each type of scattering events. The plurality of types of the scattering events include the scattering events occurred in the scanning target and the scattering events occurred in the detector In some embodiments, each of the plurality of detector layers corresponds to the first energy window or the second energy window.

In some embodiments, after determining the plurality of second energy windows in the second region, the method may further include: obtaining a depth of interaction of the photons by the detector of the PET system; and determining a region and an energy window corresponding to the photons based on the depth of interaction of the photons. The region is the first region or the second region, and the energy window is the first energy window corresponding to the first region or the second energy window corresponding to the second region.

According to the embodiments of the present disclosure, a PET system is provided, the PET system may include a PET detector and a processing unit, and the PET detector may be configured to obtain a depth of interaction of photons.

The processing unit may be configured to obtain an absorption depth curve of photons of the PET detector of the PET system, divide the detector into a first region and a second region along a depth direction of the detector based on the absorption depth curve. The detector may include a plurality of detector layers, and the depth direction of the detector may be a direction of the plurality of detector layers away from a scanning target; the processing unit may be configured to determine a first energy window in the first region to screen scattering events occurred in the scanning target; the processing unit may be configured to determine a plurality of second energy windows in the second region to retain scattering events occurred in the detector. The plurality of second energy windows may be sequentially widened in the depth direction.

According to some embodiments of the present disclosure, a device for screening scattering events is provided, the device may include an obtaining module, a first determining module, and a second determining module. The obtaining module may be configured to obtain an absorption depth curve of photons of a detector of a PET system, divide the detector into a first region and a second region along a depth direction of the detector based on the absorption depth curve. The detector may include a plurality of detector layers, and the depth direction of the detector may be a direction of the plurality of detector layers away from a scanning target; the first determining module may be configured to determine a first energy window in the first region to screen scattering events occurred in the scanning target; and the second determining module may be configured to determine a plurality of second energy windows in the second region to retain scattering events occurred in the detector. The plurality of second energy windows may be sequentially widened in the depth direction.

According to some embodiments of the present disclosure, an electronic device is provided, the electronic device may include a memory, a processor, and computer instructions stored on the memory and may be operated on the processor, when executing the computer instructions, the processor may implement a method for screening scattering events described above.

According to some embodiments of the present disclosure, a non-transitory computer-readable storage medium is provided, the storage medium may store the computer instructions, and the computer instructions, when executed by a processor, may implement a method for screening scattering events described above.

Compared to related technology, the method for screening scattering events provided by the embodiments of the present disclosure may include obtaining the absorption depth curve of the detector of the photons of the PET system, dividing the detector into the first region and the second region along the depth direction of the detector based on the absorption depth curve; determine the first energy window in the first region to screen scattering events occurred in the scanning target; and determining the plurality of second energy windows in the second region to retain the scattering events occurred in the detector. The method for screening scattering events may address a problem that the method of determining the energy windows in the related technology is unable to differentiate between two kinds of scattering coincidence events thereby causing the sensitivity of the PET system to be lower, and may reduce a screen of scattering events occurred in the detector such that improve the sensitivity of the PET system. The detector may include the plurality of detector layers, and the depth direction of the detector may be a direction of the plurality of detector layers away from a scanning target, and the plurality of second energy windows may be sequentially widened in the depth direction The details of one or more embodiments of the present disclosure are illustrated in the following accompanying drawings and descriptions to make the other features, purposes, and advantages of the present disclosure more concise and understandable.

BRIEF DESCRIPTION OF THE DRAWING

The present disclosure is further described in terms of exemplary embodiments. These exemplary embodiments are described in detail with reference to the drawings. These embodiments are non-limiting exemplary embodiments, where like reference numerals represent similar structures throughout the several views of the drawings, and wherein:

FIG. 5 is a flowchart illustrating a method for determining an upper limit and a lower limit of a target energy window according to some embodiments of the present disclosure;

FIG. 6 is a flowchart illustrating a method for dividing a first region and a second region according to some embodiments of the present disclosure;

DETAILED DESCRIPTION

Figure 1:
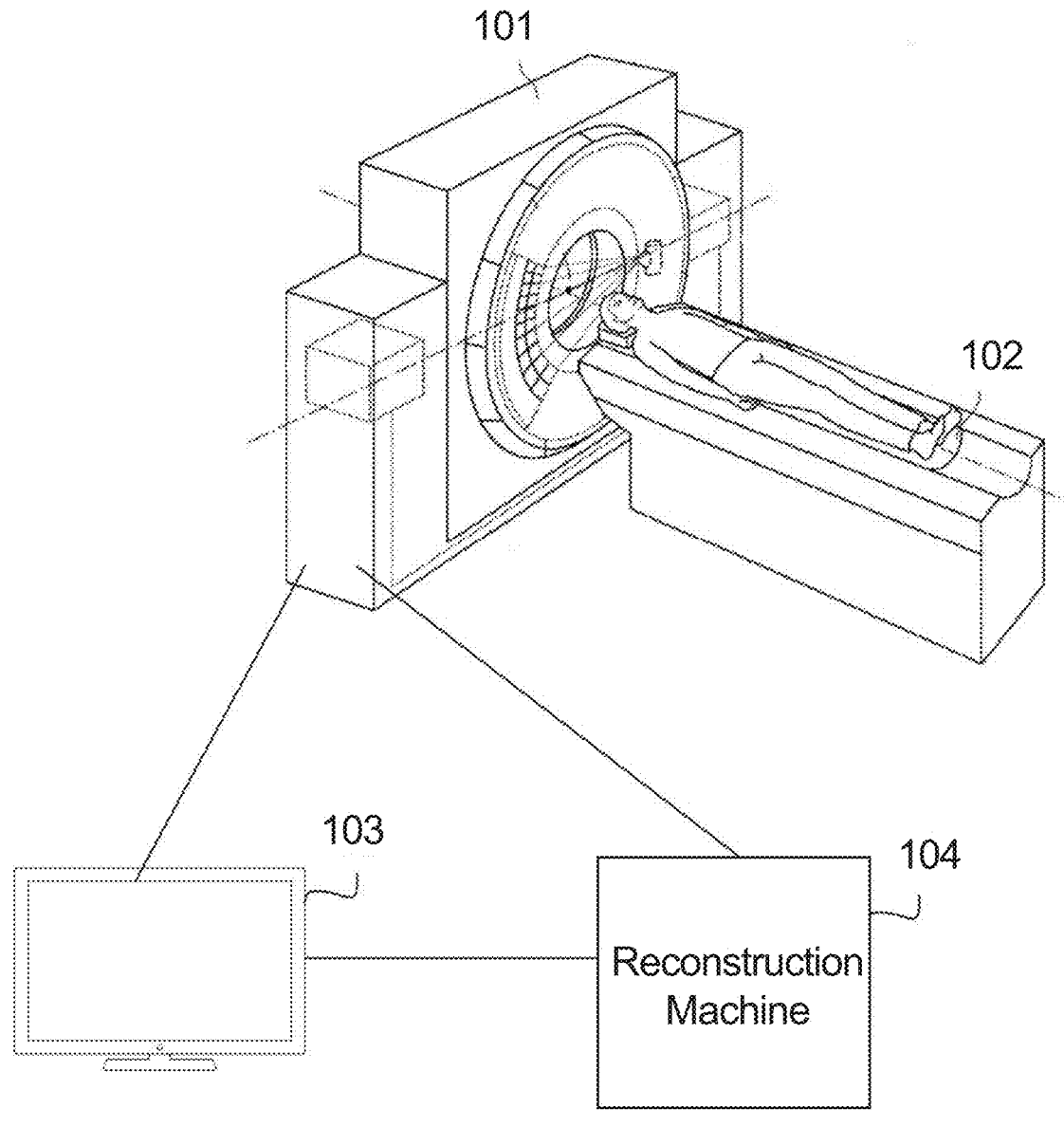
FIG. 1 is a schematic diagram illustrating an application scenario for screening scattering events according to some embodiments of the present disclosure.

To make the purposes, technical solutions and advantages of the present disclosure more clearly understood, the present disclosure is described and illustrated hereinafter in conjunction with the brief description of the drawing and the embodiments. it should be understood that the specific embodiments described herein are only for explaining the present disclosure and are not intended to limit the present disclosure. Based on the embodiments provided in the present disclosure, all other embodiments obtained by those skilled in the art without creative labor fall in the scope of protection of the present disclosure. In addition, it is also understood that although the efforts made in the development process may be complex and lengthy, some design, manufacturing or production changes based on the technical contents disclosed in the present disclosure are just conventional technical means for those skilled in the art related to the contents disclosed in the present disclosure, and should not be construed as the inadequacy of the contents disclosed in the present disclosure.

The terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Unless otherwise defined, all technical and scientific terms used herein have the same meaning as commonly understood by those skilled in the art belonging to the present disclosure. The words "one", "a", "a kind", "the" and the like in the present disclosure do not imply a limitation of quantity. The terms "one", "one", "a", "the", "the" and similar terms do not indicate a limitation of quantity and may denote the singular or plural. the terms "may include", "comprises", "has", and any variations thereof, as used in the present disclosure, are intended to cover non-exclusive compositions; e.g., processes, methods, or methods that include a series of steps or modules (units). for example, a process, method, system, product or apparatus that may include a series of steps or modules (units) is not limited to the listed steps or units, but may also include steps or units that are not listed, or may also include other steps or units that are inherent to the process, method, product or apparatus, the present disclosure does not limit the terms "connected", "connected", "coupled" and the like to physical or mechanical connections, but may include electrical connections, whether direct or indirect. direct or indirect. as used in the present disclosure, "more than one" means more than or equal to two. The term "and/or" describes an association relationship of the associated objects and indicates that three types of relationships may exist, for example, "a and/or b" may indicate that a alone exists, both a and b exist, and b alone exists. the terms "first", "second", "third" and the like in the present disclosure are merely used to distinguish similar objects, and do not represent a specific ordering of the objects.

A method for screening scattering events provided in the present disclosure may be applied in an application environment as shown in FIG. 1, FIG. 1 is a schematic diagram illustrating an application scenario of a method for screening scattering events according to some embodiments of the present disclosure. As shown in FIG. 1, the PET system may include a scanning device 101, a scanning bed 102, a host computer 103, and a reconstruction machine 104, a user may control the scanning device 101 to scan a scanning object on the scanning bed 102 through the host computer 103. The host computer 103 may send obtained scan data to the reconstruction machine 104 for image reconstruction, and ultimately may obtain a scanned image, but scattering events in a PET system may affect the quality of the scanned image, and the scanned object may be a human body or an animal.

Figure 2:
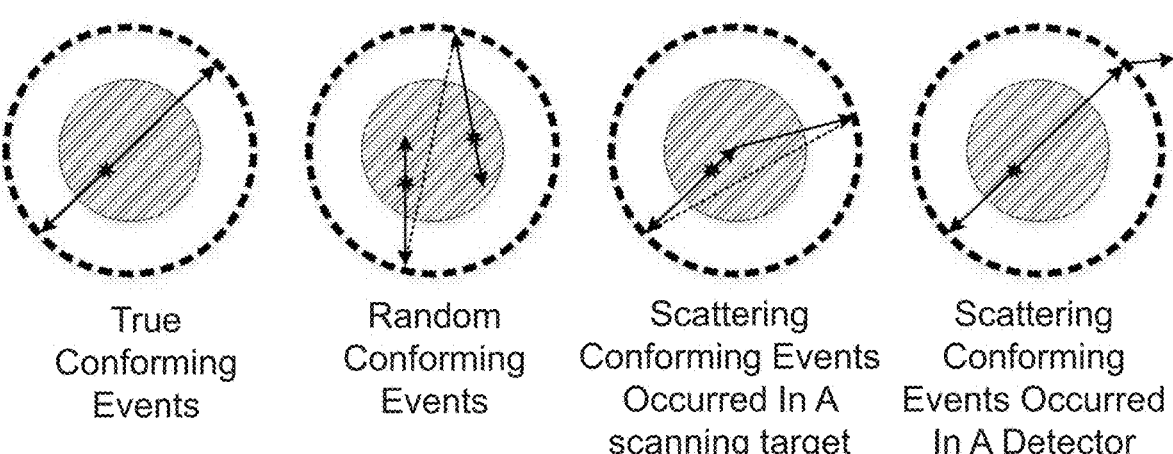
FIG. 2 is a schematic diagram illustrating a coincidence event according to some embodiments of the present disclosure.

Specifically, a same pair of γ photons may move along opposite directions and may be received by a detection unit of the PET system, thereby obtaining a coincidence event. A moving path of the pair of γ photons may be referred to as a response line, and two detection units receiving the pair of γ photons may be located at two ends of the response line. FIG. 2 is a schematic diagram illustrating a coincidence event according to some embodiments of the present disclosure. As shown in FIG. 2, a shaded portion is a field of view (FOV) of the PET system, where scattering events occurred in the scanning target may be observed, and an outer rounded box may denote a detector layer. In a scanning process based on the PET system, the coincidence events are generally categorized into three types: true coincidence events, random coincidence events, and scattering coincidence events. The same pair of γ photons are received by two detectors located on the same response line, which may be referred to as a true coincidence event. The two γ photons that do not originate from a same annihilation but are determined by the detector to originate from the same annihilation, which may be referred to as a random coincidence event. The two γ photons generated by the annihilation where at least one of the two γ photons scatters but the detector still succeeds in receiving the two γ photons may be referred to as a scattering coincidence event or a scattering event for short. Further, the scattering events may include scattering events occurred in the scanning target and scattering events occurred in the detector. To improve a signal-to-noise ratio of the scanned image, the PET system needs to capture as many of the true coincidence events, as few of the random coincidence events, and the scattering events as possible.

The scattering events of γ photons in a field of view (FOV) of the PET system may cause errors in positioning of a line of response (LOR) in the PET system, which may in turn reduce the signal-to-noise ratio of the data and deteriorate the quality of the scanned image. To avoid the effect of the scattering events on a PET scanned image, the PET system may reject scattering events by judging an energy of γ photons. In the related technology, after the detector of the PET system is calibrated for homogenization, the same "energy window" may be used for all detectors to determine a conformity of γ-photon energy. Usually, a lower limit of the γ-photon energy window may be 400 keV-450 keV, and the upper limit may be 630 keV-750 keV, therefore the sensitivity of the PET system may be relatively low. It should be noted that in the actual measurement process, the energy of γ photons may be distributed with 511 keV as a center value, therefore it is necessary to determine the energy windows of different widths according to a distribution of the energy of the γ photons.

Figure 3:
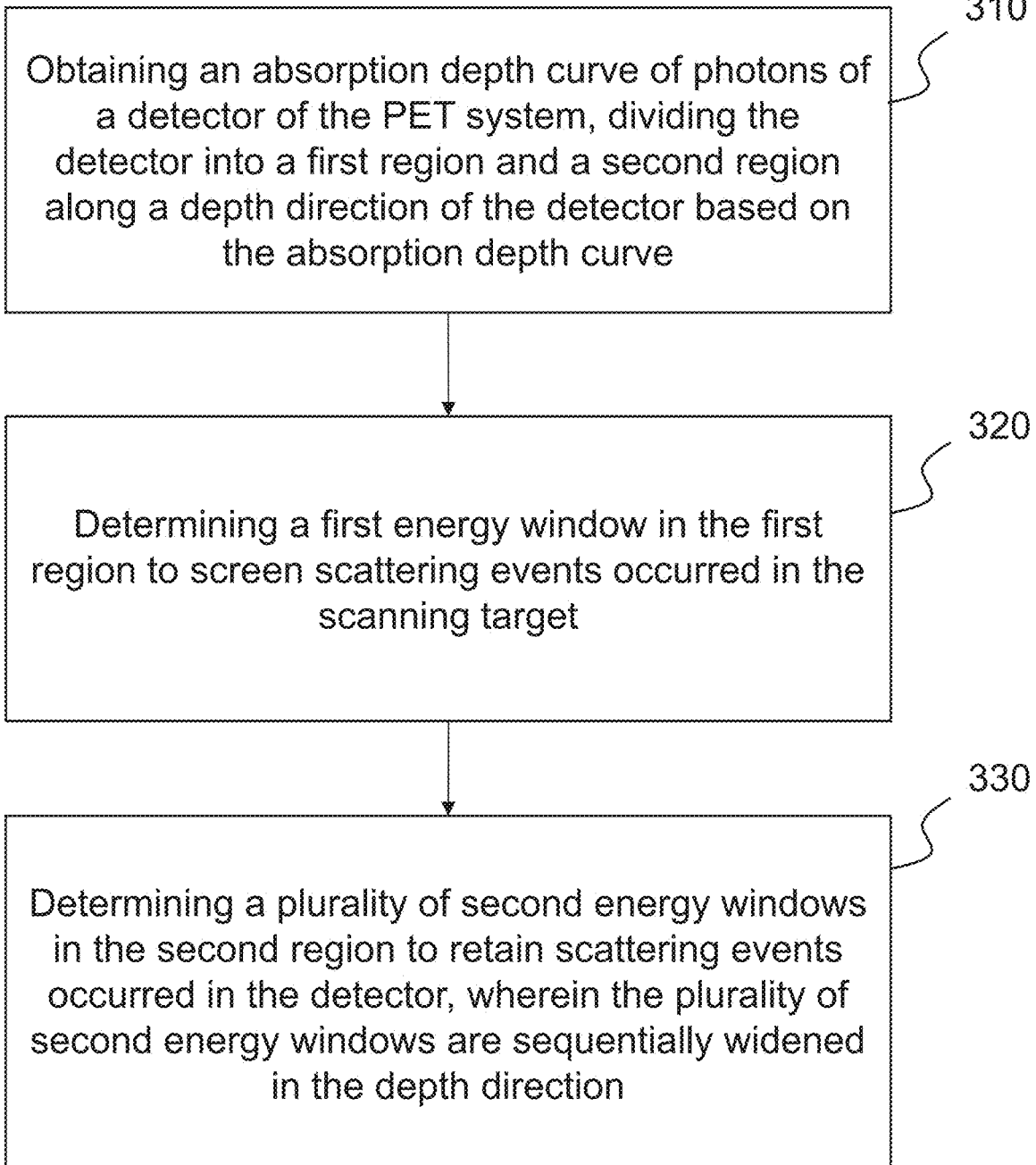
FIG. 3 is a flowchart illustrating a method for screening scattering events according to some embodiments of the present disclosure.

The present embodiment provides a method for screening scattering events. FIG. 3 is a flowchart illustrating a method for screening scattering events according to some embodiments of the present disclosure. As shown in FIG. 3, the method may include:

In 310, an absorption depth curve of photons of a detector of the PET system is obtained, and the detector is divided into a first region and a second region along a depth direction of the detector based on the absorption depth curve.

It should be noted that the detector of the PET system may include a plurality of detector layers, and the depth direction of the detector may be a direction of the plurality of detector layers away from the scanning target, so that a depth value of the detector layers close to the FOV may be relatively low, and the depth value of the detector layers away from the FOV may be relatively high, and the photons in the present disclosure may optionally be γ photons.

Figure 4:
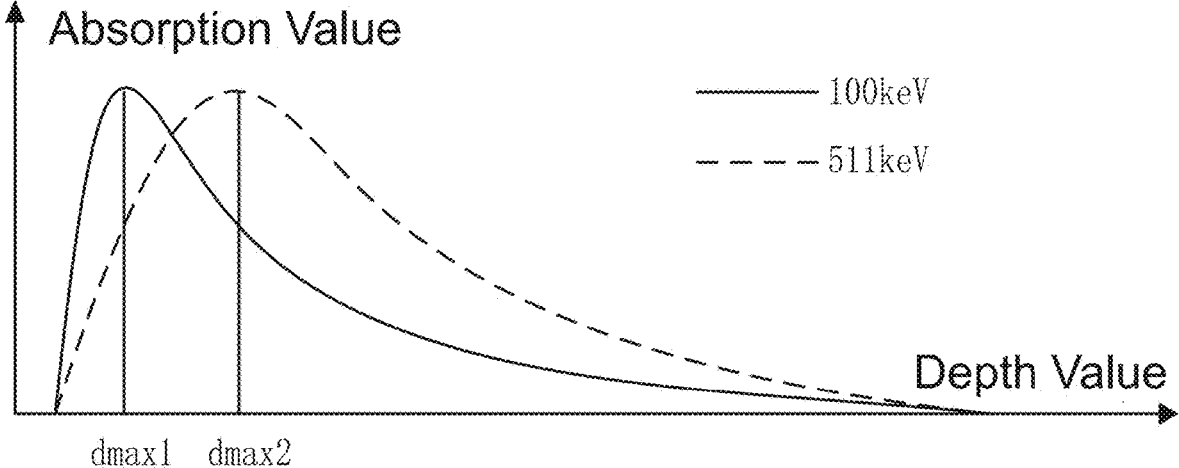
FIG. 4 is a schematic diagram illustrating an absorption depth curve according to some embodiments of the present disclosure.

The absorption depth curve may be a curve where an absorption value of the detector for a large number of photons changes with depth. FIG. 4 is a schematic diagram illustrating the absorption depth curve according to some embodiments of the present disclosure. As shown in FIG. 4, as the depth increases, the absorption value first rises and then decreases, and when energies of the photons are different, a peak of the absorption depth curve changes, e.g., in FIG. 4, a solid line is an absorption depth curve of 100 keV, and a dashed line is an absorption depth curve of 511 keV, and the depths corresponding to the both at the peak of the curves are dmax1 and dmax2, respectively. Further, any one of the values between dmax1 and dmax2 may be determined as a criterion for dividing the first region and the second region. In other embodiments, the absorption depth curve may also be selected with other energy values as desired, such as 500 keV, 600 keV, and the like.

Therefore, the present disclosure may process the photons of different energies by dividing the detector into the first region and the second region according to the depth values corresponding to the peaks of the absorption depth curves.

In 320, the first energy window in the first region is determined to screen scattering events occurred in the scanning target.

The scattering events occurred in the scanning target are scattering events that may be observed in the FOV, and since a portion of the scattering events affect the positioning of the response line, an imaging quality of the scanned image is reduced such that the portion of the scattering events need to be screened and sifted out.

In 330, a plurality of second energy windows in the second region are determined to retain scattering events occurred in the detector, and the plurality of second energy windows may be sequentially widened in the depth direction.

Accordingly, the scattering events occurred in the detector may not affect the position of the response line and so that needs to be retained to improve a signal-to-noise ratio of the scanned image.

The photons may lose a portion of energy after being scattered, so that the energy of the photons scattered inside the scanning target may be lower than 511 keV when reaching an end face of the detector, and the energies of the photons scattered inside the detector may be still 511 keV when reaching the end face of the detector. The penetration ability of the photons may be directly proportional to the energies of the photons, and the higher the absorption values of the photons are, the more the energies of the photons that are absorbed are, and the less the energies of the photons are, and the penetration ability may also be decreased. From a trend of the absorption depth curves of the photons, it may be seen that the penetration energies of the photons scattered in the FOV are weaker than the energies of the photons scattered in the detector due to energy loss. And the proportion of photons with high energy may increase along a depth direction away from the FOV.

Therefore, after dividing the first region and the second region, different energy windows may be determined for the first region and the second region to perform targeted selections for the photons. In this embodiment, the first energy window may be determined according to an actual situation, and the first energy window may be narrower than an energy window that is determined first in the second energy window, or may be wider than the energy window that is determined first in the second energy window, and the energy window that is determined first in the second energy window is an energy window that is closest to the FOV in the second energy window. On the other hand, for a plurality of second energy windows, the widths of the energy windows increase along the depth direction to retain more photons with high energy.

Through the above operations 310 to 330, the present embodiment may determine a first energy window and the plurality of second energy windows that are sequentially widened in the depth direction of the detector, retain the scattering events occurred in the detector while screening the scattering events occurred in the scanning target, such that may address the problem that the method of determining the energy window in the related technology is unable to distinguish between two types of scattering coincidence events thereby causing the sensitivity of the PET system to be relatively low, and the present embodiment may reduce the screen of the scattering events occurred in the detector, and improve the sensitivity of the PET system.

In some embodiments, since the detector may include a plurality of detector layers, each of the plurality of detector layers may correspond to one first energy window or one second energy window. When there is a plurality of first energy windows, the upper limits and the lower limits of each of the plurality of first energy windows may be different, and when there is a plurality of second energy windows, the plurality of second energy windows may be sequentially widened in the depth direction. In the present embodiment, an energy window may be determined in each of the plurality of detector layers, which may screen or retain the scattering events accurately, and further improve the sensitivity of the PET system.

In some embodiments, the PET system may include a detector that may obtain a depth of interaction (DOI) of the photons. Specifically, the detector that performs DOI detection may be formed by layering individual scintillation crystals along the depth direction and solving coordinate information of the DOI by a center of gravity operation to improve a spatial resolution in the depth direction. A count of layers of the DOI detector may be a count of layers of scintillator elements layered along the depth direction. After obtaining the DOI information, a depth and an absorption of the photons at the depth may be determined based on the DOI information, and then the absorption depth curve of the photons may be obtained.

Further, when the first energy window and/or the second energy window are determined regarded as a target energy window, an upper limit and a lower limit of the target energy window are obtained based on a detector parameter of the detector. The upper limit and the lower limit of the target energy window may be configured to determine a range of the target energy window, the detector parameter may include at least one of: an energy resolution of the detector in the plurality of detector layers, a material type of a scintillation crystal in the detector, a size of the scintillation crystal, or a resolution of a depth of interaction for the photons in the PET system.

First, the energy resolution may be a detection accuracy of the energy of the photons of the detector, and a level of the energy resolution may affect a determination accuracy of the upper limit and the lower limit of the energy window. Second, the materials of the scintillation crystals are different, and the energies lost by the photons when scattered in the materials of the scintillation crystals are also different, thereby affecting the values of the upper limit and the lower limit of the target energy window. The materials of the scintillation crystal may include, such as, a bismuth germanate (BGO) crystal and a Lutetium oxyorthosilicate (LSO) crystal. Further, the material type of the scintillation crystal may also affect the energy resolution of the detector; again, the smaller the size of the scintillation crystal, the higher the probability of the scattering events occurred in the scintillation crystal, and in an overall count of scattering events, a ratio of the scattering events occurred in the scanning target to the scattering events occurred in the detector may also change. Accordingly, the values of the upper limit and the lower limit of the target energy window may also change. Therefore, even in response to determining that the material types of the scintillation crystal are the same and the DOI resolution may be the same, to achieve the best results, the target energy windows need to be changed according to the size of the scintillation crystal. Lastly, for scintillation crystals of the same size and the same material type, in response to determining that the DOI resolution of the detector is different, e.g., 1 mm and 5 mm, then a division of the first region and the second region of the detector may be different, and the upper limit and the lower limit of the target energy window may be different.

Therefore, the upper limit and the lower limit of the target energy window may be determined based on the detector parameter, which may improve the accuracy of determining the energy window.

Further, when determining the target energy window according to the above detector parameter, the upper limit and the lower limit of the target energy window may be determined by simulating an entire PET system and determining the upper limit and the lower limit of the target energy window according to a simulation result, and experimental collecting data may be obtained using an actual PET system, and then an optimal upper limit and an optimal lower limit of the target energy window may be obtained by performing an iteration calculation based on indicators such as the sensitivity of the PET system, a scattering fraction, and a noise equivalent count rate (NECR), etc.

FIG. 5 is a flowchart illustrating a method for determining an upper limit and a lower limit of a target energy window according to some embodiments of the present disclosure. As shown in FIG. 5, the method may include:

In 510, an initial value of the upper limit and an initial value of the lower limit are determined according to the detector parameter, and an initial energy window is determined based on the initial value of the upper limit and the initial value of the lower limit.

For a well-designed PET system, the detector parameter may be all determined, so that the initial value of the upper limit and the initial value of the lower limit may be determined based on the energy resolution of the detector, the material type of the scintillation crystal in the detector, the size of the scintillation crystal, and the resolution of the depth of interaction of the photons in the PET system, and thereby obtaining the initial energy window.

In 520, a system parameter of the PET system is determined based on the initial energy window. The system parameter may include at least one of the sensitivity and the NECR.

Specifically, a calculation of the system parameter in the present embodiment may be realized by a simulation algorithm, and a target of a simulation calculation target may include the system parameter of the sensitivity and/or the system parameter of the NECR.

In 530, the upper limit and the lower limit of the initial energy window are updated based on the system parameter, and an iteration calculation may be performed on the system parameter based on an updated initial energy window.

In response to determining that the system parameter is not in a preset threshold range, it means that the upper limit and the lower limit of the initial energy window may not be satisfied at this time, and the upper limit and the lower limit need to be reset. An update of the upper limit and the lower limit may be realized according to the system parameter obtained by simulation calculation, for example, a correspondence between the upper limit and the system parameter, a correspondence between the lower limit and the system parameter may be pre-determined respectively, and after the system parameter is obtained by performing the simulation calculation, the upper limit and the lower limit of the initial energy window may be increased or decreased according to the above correspondence.

In 540, in response to determining that the system parameter is within a preset threshold range, the updated upper limit and the updated lower limit are determined as the upper limit and the lower limit of the target energy window, and the preset threshold range may be determined based on the detector parameter.

Accordingly, in response to determining that the system parameters are in a preset threshold range, it means that the upper limit and the lower limit of the initial energy window satisfy the requirements at this time, and the iteration calculation may be ended.

Through the above operations 510 to 540, the present embodiment may determine an accurate upper limit and lower limit of the target energy window based on the iteration calculation using the system parameter as a standard.

In some embodiments, FIG. 6 is a flowchart illustrating a method for dividing a first region and a second region according to some embodiments of the present disclosure. As shown in FIG. 6, the method may include:

In 610, a proportion of each type of different types of scattering events is determined based on the absorption depth curve. The types of the scattering events may include the scattering events occurred in the scanning target and the scattering events occurred in the detector.

Typically, only about 40% of the photons captured by the scintillation crystal in the detector may deposit all of the 511 keV energy in the scintillation crystal. The remaining 60% of the photons may deposit a portion of the energy in a range of tens of keV to 400 keV, and typically in a PET system energy conformity discrimination processing, the coincidence event corresponding to the 60% of the photons may be determined as the scattering events, and thereby being rejected.

When the detector is capable of obtaining the DOI information, according to the statistical rule, the proportion of the scattering events occurred in the scanning target may be relatively high among the scattering events captured by the detector layers close to the FOV end. Along a direction of the plurality of detector layers away from the scanning target, the proportion of the scattering events occurred in the scanning target may decrease gradually, and the proportion of scattering events occurred in the detector scintillation crystal may increase gradually. Therefore, the scattering events may be zoned and screened using the absorption depth curve determined based on the DOI information.

In 620, the detector is divided into the first region and the second region along the depth direction of the detector based on the proportion of each type of scattering events.

In a region where a high proportion of scattering events occurred in the scanning target, the data may be ensured to maintain a high signal-to-noise ratio using a strict energy window. In a region where a high proportion of scattering events occurred in the detector, the sensitivity of the PET system may be improved using a relaxed energy window.

In the present embodiment, a proportion of the scattering events obtained when dividing the first region and the second region may be determined empirically, or may be obtained by a simulation algorithm or a deep learning network model through training. Specifically, a region where the proportion of the scattering events occurred in the scanning target is greater than or equal to the proportion of the scattering events occurred in the detector may be determined as a first region corresponding to a smaller range of the first energy window to screen the scattering events occurred in the scanning target. A region where the proportion of scattering events occurred in the scanning target is smaller than the proportion of scattering events occurred in the detector may be determined as a second region corresponding to a larger range of the second energy window to retain the scattering events occurred in the detector.

Through the above operations 610 and 620, the first region and the second region may be divided based on the proportion of each type of plurality of scattering events, a processing to the scattering events may be determined directly, and an efficiency of determining the first energy window and the second energy window may be improved.

After the first energy window and the second energy window of the detector are determined, the photon scattering events during the actual scanning process may be screened. Specifically, the depth of interaction of the photons in the PET system may be obtained by the detector. Then, a region corresponding to the photons and an energy window corresponding to the photons may be determined based on the depth of interaction of the photons. The region may be a first region or a second region. The energy window may be a first energy window corresponding to the first region or a second energy window corresponding to the second region. The depth of interaction of the photons may be a direct depth of interaction of the photons of the detector of the PET system or an incident depth of interaction of the photons accurately determined according to the response line. The direct depth of interaction may be a distance from scattering positions of the photons to an inner edge of the scintillation crystal of the detector. The depth of interaction determined accurately based on the response line may be a distance from an intersection point of a line connecting two action points in the coincidence events and the inner edge of the scintillation crystal to an action point. The manner of obtaining the depth of interaction of the photons may include using spectroscopy, using multiple layers of scintillation crystals of different materials, using a double-ended readout, and using a multi-channel readout of continuous scintillation crystals. Since the first region and second region and the first energy window and second energy window are divided in the depth direction of the detector in advance, the regions and energy windows corresponding to the depth of intersection of the photons may be determined based on the depth of interaction of the photons. In this embodiment, the screening accuracy of the photons may be improved based on the energy windows with different ranges as described above.

Further, since the absorption depth curves of photons of different energies may represent different ratios of the scattering events, in a process of dividing the first energy window and the second energy window, a target ratio of the scattering events may be preset first, and after dividing the first region and the second region according to the absorption depth curves and obtaining the initial ratio of the scattering events, the initial ratio may be adjusted by determining a width of the first energy window and a width of the second energy window to the target ratio.

The embodiments of the present disclosure are described and illustrated below by way of optional embodiments.

The PET system having an ability to obtain DOI information may determine a 4 m×4 mm×20 mm LYSO (Yttrium-lutetium Orthosilicate) crystal as the scintillation crystal of the detector, and in the process of using the PET system, different energy window ranges may be determined based on the DOI depth information to perform an energy conforming determination. Specifically, a stringent first energy window may be used on a side close to the FOV, such as 450 keV-650 keV. A plurality of more relaxed second energy windows may be used on a side away from the FOV, and the plurality of second energy windows may be sequentially widened in the depth direction, such as 300 keV-700 keV, 200 keV-800 keV, 100 keV-900 keV, and the like.

In this embodiment, the detector may be divided into a first layer, a second layer . . . a $n^{th}$ layer along the depth direction of the detector based on the DOI information, and each layer may be provided with an independent energy window, and the independent energy window may be a first energy window or a second energy window. During the scanning process, the PET system may determine an action position of the γ photons in a $i^{th}$ layer of the detector based on the DOI information, and an energy determination may be performed on the scattering event using the energy window of the $i^{th}$ layer, where i ∈[1, n]. A determination rule of the energy windows of each of the plurality of detector layers may be specified as the energy window of the second layer may be the tightest, and the energy window of the third layer . . . and the energy window of the $n^{th}$ layer may be sequentially widened in the depth direction, at which time, the second layer to the $n^{th}$ layer may be the second energy windows, and the energy window of the first layer that is determined as the first energy window may be determined independently, and the energy window of the first layer may be tighter or wider than the energy window of the second layer or may be determined as an energy window as same as the energy window as the second layer.

In other embodiments, the division of the first region and the second region may be jointly determined by a precision of the DOI and the absorption depth curve of the γ photons in the crystal, and when the precision of the DOI is sufficiently high, the first energy window needs to be determined independently for the first layer to the $x^{th}$ layer, respectively, and the $x^{th}$ layer may onwards correspond to a progressively enlarged second energy window, x ∈[1, n].

In PET systems, the sensitivity is a more important index, and a process for improving the sensitivity without reducing the signal-to-noise ratio of the system may usually include increasing a thickness of the scintillation crystal, increasing an axial length of a detector ring, and the like, but all of the above measures may cause a significant increase in the cost of the PET system. In the present embodiment, the positions and the types of scattering events may be distinguished by using the depth curve information of the γ photons and the DOI information provided by the detector, which may reduce the probability that the scattering events occurred in the detector are treated as the scattering events occurred in the scanning target and then screened, and the scattering events occurred in the detector may be retained due to screening of scattering events occurred in the scanning target, and at the same time, the present embodiment may improve the software algorithm such that improve the sensitivity of the PET system and ensure the signal-to-noise ratio of system data without increasing the cost.

It should be noted that the operations illustrated in the above flow or the flowchart may be executed in a computer system, such as a set of computers capable of executing instructions, and, although a logical sequence is illustrated in the flowchart, the operations illustrated or described may be performed in a different order from the logical sequence shown or described herein in some instances.

Figure 7:
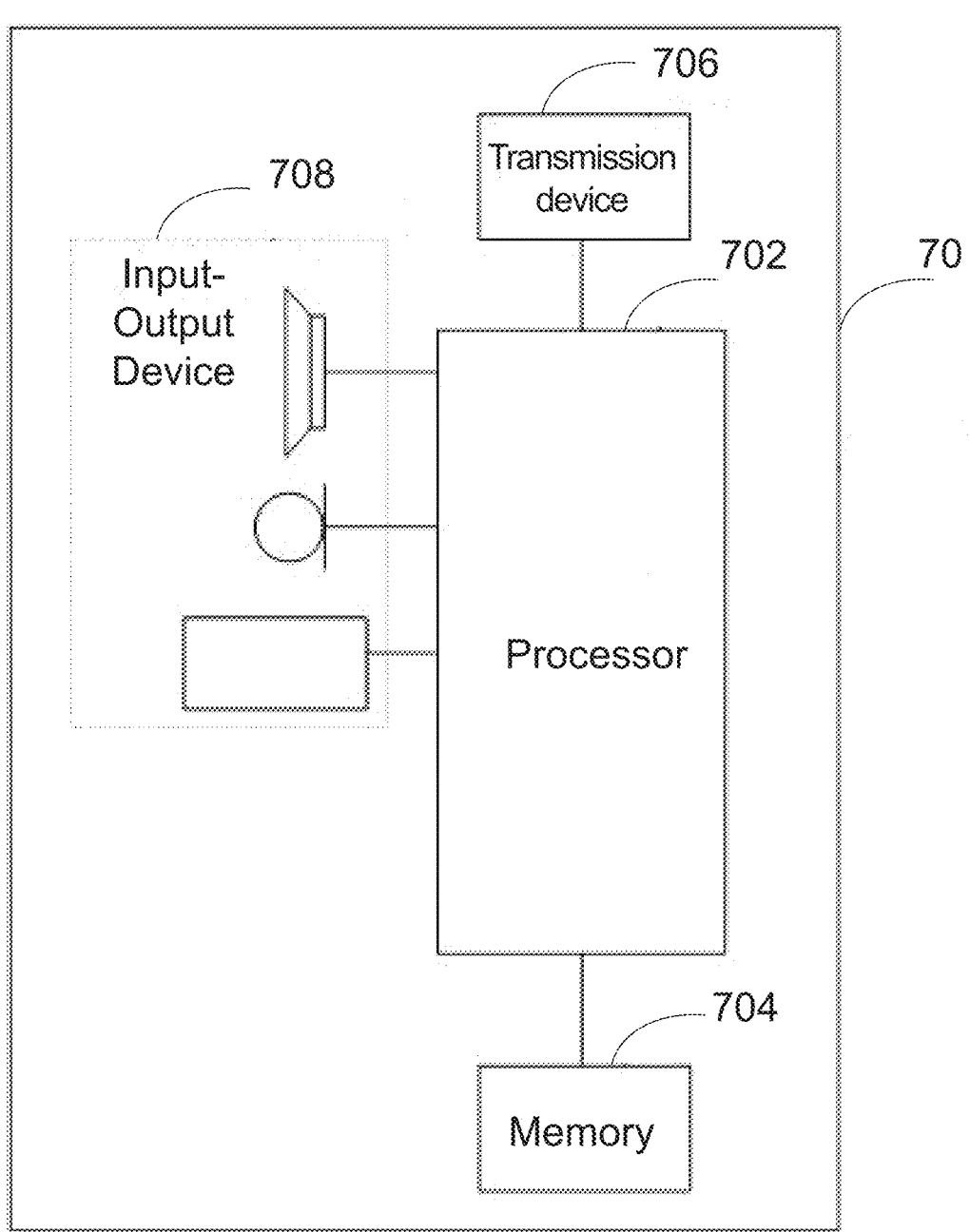
FIG. 7 is a block diagram illustrating a hardware structure of a terminal for screening scattering events according to some embodiments of the present disclosure.

The method embodiments provided in the present disclosure may be executed in a terminal, a computer, or a similar computing device. Taking the method operated on a terminal as an example, FIG. 7 is a block diagram illustrating a hardware structure of a terminal for screening scattering events according to embodiments of the present disclosure. As shown in FIG. 7, a terminal 70 may include one or more (only one processor 702 is shown in FIG. 7) processors 702 (the processor 702 may include, but is not limited to, a processing device such as a microprocessor MCU or a programmable logic device FPGA, etc.) and a memory 704 configured to store data. Optionally, the terminal 70 may also include a transmission device 706 for communication functions and an input-output device 708. Those skilled in the art may understand that the structure shown in FIG. 7 is merely schematic, and does not limit the structure of the above terminal. For example, the terminal 70 may also include more or fewer components than shown in FIG. 7, or may have a different configuration than shown in FIG. 7.

The memory 704 may be configured to store a control program, e.g., a software program of an application software and a module of the application software, such as a control program corresponding to the method for screening scattering events in the present disclosure embodiment. The processor 702 may execute various functional applications and data processing by operating the control program stored in the memory 704, i.e., realizing the above method. The memory 704 may include a high-speed random memory, and may also include a non-volatile memory, such as one or more magnetic storage devices, a flash memory, or other non-volatile solid-state memory. In some examples, the memory 704 may further include one or more memories remotely arranged relative to the processor 702, and these remote memories may be connected to the terminal 70 via a network. The examples of the above networks may include, but are not limited to, an Internet, an enterprise intranet, a local area network, a mobile communication network, and combinations thereof.

The transmission device 706 may be configured to receive or send data via a network. The specific examples of the network described above may include a wireless network provided by a communications provider of the terminal 70. In one example, the transmission device 706 may include a network interface controller (NIC) that may be connected to other network devices via a base station and thus may communicate with the Internet. In one example, the transmission device 706 may be a radio frequency (RF) module configured to communicate with the Internet wirelessly.

The present embodiments also provide a device for screening scattering events, which may be configured to realize the above embodiments and optional embodiments, which have already been described without further elaboration. As used hereinafter, the terms "module", "unit", "sub-unit", and the like may be a combination of software and/or hardware that implements a preset function. Although the devices described in the following embodiments may be preferably implemented in software, the implementation of hardware, or a combination of software and hardware, may be possible and contemplated.

Figure 8:
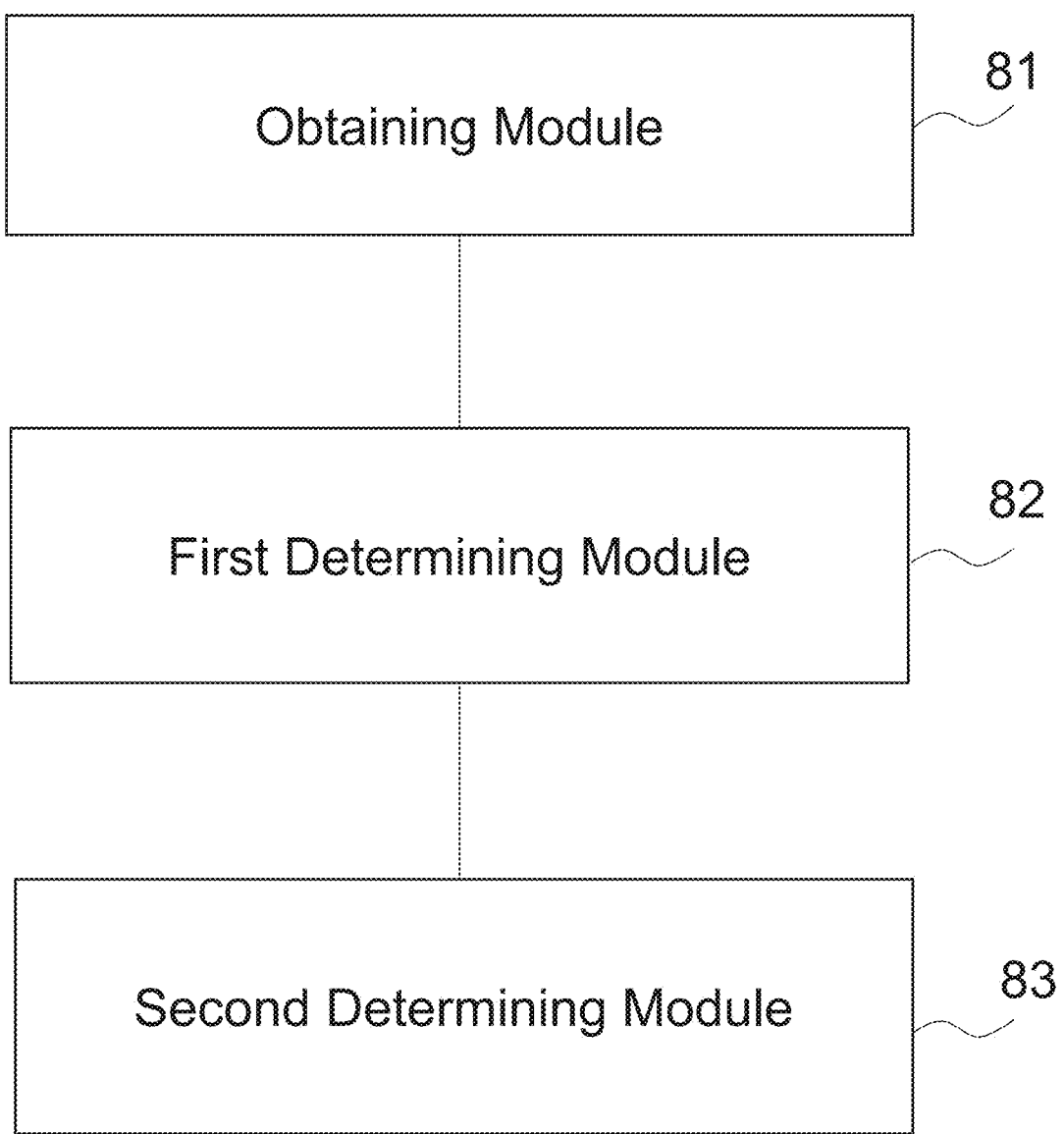
FIG. 8 is a block diagram illustrating a structure of a device for screening scattering events according to some embodiments of the present disclosure.

FIG. 8 is a block diagram illustrating a structure of a device for screening scattering events according to some embodiments of the present disclosure. As shown in FIG. 8, the device may include an obtaining module 81, a first determining module 82, and a second determining module 83.

The obtaining module 81 may be configured to obtain an absorption depth curve of photons of a detector of a PET system, divide the detector into a first region and a second region along a depth direction of the detector based on the absorption depth curve, the detector may include a plurality of detector layers, and the depth direction of the detector may be a direction of the plurality of detector layers away from a scanning target. The PET system may include a detector capable of obtaining a depth of interaction of photons, the absorption depth curve may be obtained based on the depth of interaction of the photons.

The first determining module 82 may be configured to determine a first energy window in the first region to screen scattering events occurred in the scanning target.

The second determining module 83 may be configured to determine a plurality of second energy windows in the second region to retain scattering events occurred in the detector, and the plurality of second energy windows may be sequentially widened in the depth direction.

The present embodiment may determine one or more first energy windows and the plurality of second energy windows that are sequentially widened in the depth direction of the detector, retain the scattering events occurred in the detector while screening the scattering events occurred in the scanning target, such that may address the problem that the method of determining the energy window in the related technology is unable to distinguish between two types of scattering coincidence events thereby causing the sensitivity of the PET system to be relatively low, and the present embodiment may reduce the screen of the scattering events occurred in the detector, and improve the sensitivity of the PET system.

In some embodiments, the first determining module 82 and/or the second determining module 83 may be further configured to obtain an upper limit and a lower limit of a target energy window based on a detector parameter, and the target energy window may include the first energy window and/or the second energy window, and the detector parameter may include at least one of: an energy resolution of the detector in the plurality of detector layers, a material type of a scintillation crystal in the detector, a size of the scintillation crystal, or a resolution of a depth of interaction of photons in the PET system.

In some embodiments, the first determining module 82 and/or the second determining module 83 may be further configured to determine an initial value of the upper limit and an initial value of the lower limit according to the detector parameter; determine an initial energy window based on the initial value of the upper limit and the initial value of the lower limit; determine a system parameter of the PET system based on the initial energy window; update the upper limit and the lower limit of the initial energy window based on the system parameter to obtain an updated initial energy window including an updated upper limit and an updated lower limit; perform an iteration calculation on the system parameter based on the updated initial energy window; and in response to determining that the system parameter is within a preset threshold range, determine the updated upper limit and the updated lower limit as the upper limit and the lower limit of the target energy window. The system parameter may include at least one of a sensitivity and a noise equivalent count metric, and the preset threshold range may be determined based on the detector parameter.

In some embodiments, the first determining module 82 and/or the second determining module 83 may be further configured to obtain a depth of interaction of the photons of the PET system; determine a proportion of each type of a plurality of types of scattering events based on the depth of interaction; and divide the detector into the first region and the second region along the depth direction of the detector based on the proportion of each type of scattering events. The plurality of types of the scattering events may include the scattering events occurred in the scanning target and the scattering events occurred in the detector.

In some embodiments, each of the plurality of detector layers may correspond to one first energy window or one second energy window.

The embodiments of the present disclosure also provide a PET system that may include a PET detector and a processing unit. The PET detector may be configured to obtain a depth of interaction of photons. The processing unit may be configured to obtain an absorption depth curve of photons of the PET detector of the PET system, and divide the detector into a first region and a second region along a depth direction of the detector based on the absorption depth curve. The PET detector may include a plurality of detector layers, and the depth direction of the detector may be a direction of the plurality of detector layers away from a scanning target. The processing unit may be configured to determine a first energy window in the first region to screen the scattering events occurred in the scanning target; and the processing unit is configured to determine a plurality of second energy windows in the second region to retain the scattering events occurred in the detector, and the plurality of second energy windows may be sequentially widened in the depth direction.

The present embodiment may determine one or more first energy windows and the plurality of second energy windows that are sequentially widened in the depth direction of the detector, retain the scattering events occurred in the detector while screening the scattering events occurred in the scanning target, such that may address the problem that the method of determining the energy window in the related technology is unable to distinguish between two types of scattering coincidence events thereby causing the sensitivity of the PET system to be relatively low, and the present embodiment may reduce the screen of the scattering events occurred in the detector, and improve the sensitivity of the PET system.

In some embodiments, the processing unit may be further configured to obtain an upper limit and a lower limit of a target energy window based on a detector parameter of the detector, the target energy window may include the first energy window and/or the second energy window, and the detector parameter may include at least one of: an energy resolution of the detector in the plurality of detector layers, a material type of a scintillation crystal in the detector, a size of the scintillation crystal, or a resolution of a depth of interaction of the photons in the PET system.

In some embodiments, the processing unit may be further configured to determine an initial value of the upper limit and an initial value of the lower limit according to the detector parameter, determine an initial energy window based on the initial value of the upper limit and the initial value of the lower limit; determine a system parameter of the PET system based on the initial energy window; update the upper limit and the lower limit of the initial energy window based on the system parameter to obtain an updated initial energy window including an updated upper limit and an updated lower limit; perform an iteration calculation on the system parameter based on the updated initial energy window; and in response to determining that the system parameter is within a preset threshold range, determining the updated upper limit and the updated lower limit as the upper limit and the lower limit of the target energy window. The system parameter may include at least one of a sensitivity and a noise equivalent count metric and the preset threshold range may be determined based on the detector parameter.

In some embodiments, the processing unit may be further configured to obtain a depth of interaction of the photons of the PET system; determine a proportion of each type of a plurality of types of scattering events based on the depth of interaction; and divide the detector into the first region and the second region along the depth direction of the detector based on the proportion of the each type of scattering events. The plurality of types of the scattering events may include the scattering events occurred in the scanning target and the scattering events occurred in the detector.

In some embodiments, each of the plurality of detector layers may correspond to one first energy window or one second energy window.

It should be noted that each of the above modules may be a function module or a program module, and may be realized either by software or by hardware. For the modules realized by hardware, each of the above-mentioned modules may be located in the same processor; or each of the above modules may be located in different processors according to the form of any combination.

The present embodiment further provides an electronic device that may include a memory and a processor. The memory may store computer instructions, the processor may be configured to operate the computer instructions to perform the operations in any one of the embodiments of the method described above.

In the present embodiment, the above electronic device may further include a transmission device and an input-output device. The transmission device may be connected to the processor described above and the input-output device may be connected to the processor described above.

In the present embodiment, the above processor may be configured to perform the following operations via the computer instructions:

In operation 1, an absorption depth curve of photons of a detector of the PET system is obtained, the detector is divided into a first region and a second region along a depth direction of the detector based on the absorption depth curve, the detector may include a plurality of detector layers, and the depth direction of the detector may be a direction of the plurality of detector layers away from a scanning target.

In operation 2, a first energy window in the first region is determined to screen scattering events occurred in the scanning target.

In operation 3, a plurality of second energy windows in the second region are determined to retain scattering events occurred in the detector, and the plurality of second energy windows may be sequentially widened in the depth direction.

It should be noted that specific examples in this embodiment may be referred to the examples described in the above embodiments and optional embodiments, which may not be repeated herein.

Alternatively, in conjunction with the method for screening scattering events in the above embodiments, the embodiments of the present disclosure may realize the method for screening scattering events by providing a non-transitory computer-readable storage medium. The storage medium may store computer instructions. The computer instructions, when executed by the processor, may implement any one of the methods for screening scattering events in the above embodiments.

The various technical features of the above embodiments may be combined in any combination, and all possible combinations of the various technical features of the above embodiments have not been described for the sake of conciseness of description; however, as long as there is no contradiction in the combinations of these technical features, they should be considered to be in the scope of the present disclosure.

The above embodiments express only several embodiments of the present disclosure, which are described in a more specific and detailed manner, but are not to be construed as a limitation of the patent scope of the present disclosure. It should be pointed out that for those skilled in the art, several deformations and improvements may be made without departing from the conception of the present disclosure, and these fall in the scope of protection of the present disclosure. Therefore, the scope of protection of the present disclosure shall be subject to the appended claims.

What is claimed is:

1. A method for screening scattering events, wherein the method is applied to a PET system and the method comprises:

obtaining an absorption depth curve of photons of a detector of the PET system, dividing the detector into a first region and a second region along a depth direction of the detector based on the absorption depth curve, wherein the detector includes a plurality of detector layers, and the depth direction of the detector is a direction of the plurality of detector layers away from a scanning target;

determining a first energy window in the first region to screen scattering events occurred in the scanning target; and determining a plurality of second energy windows in the second region to retain scattering events occurred in the detector, wherein the plurality of second energy windows are sequentially widened in the depth direction.

2. The method of claim 1, further comprising:

obtaining an upper limit and a lower limit of a target energy window based on a detector parameter of the detector, wherein the target energy window includes the first energy window and/or the second energy window, and the detector parameter includes at least one of:

an energy resolution of the detector in the plurality of detector layers, a material type of a scintillation crystal in the detector, a size of the scintillation crystal, or a resolution of a depth of interaction of the photons in the PET system.

3. The method of claim 2, wherein the obtaining the upper limit and the lower limit of the target energy window based on the detector parameter of the detector includes:

determining an initial value of the upper limit and an initial value of the lower limit according to the detector parameter;

determining an initial energy window based on the initial value of the upper limit and the initial value of the lower limit;

determining a system parameter of the PET system based on the initial energy window, wherein the system parameter includes at least one of a sensitivity and a noise equivalent count metric;

updating the upper limit and the lower limit of the initial energy window based on the system parameter to obtain an updated initial energy window including an updated upper limit and an updated lower limit;

performing an iteration calculation on the system parameter based on the updated initial energy window; and in response to determining that the system parameter is within a preset threshold range, determining the updated upper limit and the updated lower limit as the upper limit and the lower limit of the target energy window, wherein the preset threshold range is determined based on the detector parameter.

4. The method of claim 1, wherein the obtaining the absorption depth curve of the photons of the detector of the PET system, and dividing the detector into the first region and the second region along the depth direction of the detector based on the absorption depth curve includes:

determining a proportion of each type of a plurality of types of scattering events based on the absorption depth curve, wherein the plurality of types of the scattering events include the scattering events occurred in the scanning target and the scattering events occurred in the detector; and dividing the detector into the first region and the second region along the depth direction of the detector based on the proportion of the each type of scattering events.

5. The method of claim 1, wherein after determining the plurality of second energy windows in the second region, the method further comprises:

obtaining a depth of interaction of the photons by the detector of the PET system; and determining a region and an energy window corresponding to the photons based on the depth of interaction of the photons, wherein the region is the first region or the second region, and the energy window is the first energy window corresponding to the first region or the second energy window corresponding to the second region.

6. The method of claim 1, wherein each of the plurality of detector layers corresponds to one first energy window or one second energy window.

7. A PET system comprising a PET detector and a processing unit, wherein the PET detector is configured to obtain a depth of interaction of photons;

the processing unit is configured to obtain an absorption depth curve of photons of a PET detector of the PET system, divide the detector into a first region and a second region along a depth direction of the detector based on the absorption depth curve, wherein the detector includes a plurality of detector layers, and the depth direction of the detector is a direction of the plurality of detector layers away from a scanning target;

the processing unit is configured to determine a first energy window in the first region to screen scattering events occurred in the scanning target;

the processing unit is configured to determine a plurality of second energy windows in the second region to retain scattering events occurred in the detector, wherein the plurality of second energy windows are sequentially widened in the depth direction.

8. An electronic device comprising a memory and a processor, wherein the memory stores computer instructions; and the processor is configured to execute the computer instructions to perform the method for screening scattering events, wherein the method comprises:

obtaining an absorption depth curve of photons of a detector of a PET system, dividing the detector into a first region and a second region along a depth direction of the detector based on the absorption depth curve, wherein the detector includes a plurality of detector layers, and the depth direction of the detector is a direction of the plurality of detector layers away from a scanning target;

screening scattering events occurred in the scanning target by determining a first energy window in the first region; and retaining scattering events occurred in the detector by determining a plurality of second energy windows in the second region, wherein the plurality of second energy windows are sequentially widened in the depth direction.

9. The PET system of claim 7, wherein the processing unit is further configured to:

obtain an upper limit and a lower limit of a target energy window based on a detector parameter of the detector, wherein the target energy window includes the first energy window and/or the second energy window, and the detector parameter includes at least one of:

an energy resolution of the detector in the plurality of detector layers, a material type of a scintillation crystal in the detector, a size of the scintillation crystal, or a resolution of a depth of interaction of the photons in the PET system.

10. The PET system of claim 7, wherein to obtain the upper limit and the lower limit of the target energy window based on the detector parameter of the detector, the processing unit is configured to:

determine an initial value of the upper limit and an initial value of the lower limit according to the detector parameter;

determine an initial energy window based on the initial value of the upper limit and the initial value of the lower limit;

determine a system parameter of the PET system based on the initial energy window, wherein the system parameter includes at least one of a sensitivity and a noise equivalent count metric;

update the upper limit and the lower limit of the initial energy window based on the system parameter to obtain an updated initial energy window including an updated upper limit and an updated lower limit;

perform an iteration calculation on the system parameter based on the updated initial energy window; and in response to determining that the system parameter is within a preset threshold range, determine the updated upper limit and the updated lower limit as the upper limit and the lower limit of the target energy window, wherein the preset threshold range is determined based on the detector parameter.

11. The PET system of claim 7, wherein to obtain the absorption depth curve of the photons of the detector of the PET system, and dividing the detector into the first region and the second region along the depth direction of the detector based on the absorption depth curve, the processing unit is configured to:

determine a proportion of each type of a plurality of types of scattering events based on the absorption depth curve, wherein the plurality of types of the scattering events include the scattering events occurred in the scanning target and the scattering events occurred in the detector; and divide the detector into the first region and the second region along the depth direction of the detector based on the proportion of the each type of scattering events.

12. The PET system of claim 7, wherein after to determine the plurality of second energy windows in the second region, the processing unit is configured to:

obtain a depth of interaction of the photons by the detector of the PET system; and determine a region and an energy window corresponding to the photons based on the depth of interaction of the photons, wherein the region is the first region or the second region, and the energy window is the first energy window corresponding to the first region or the second energy window corresponding to the second region.

13. The PET system of claim 7, wherein each of the plurality of detector layers corresponds to the first energy window or the second energy window.

14. The method of claim 1, wherein a first energy window is used on a side close to a field of view (FOV) of the PET system, and a plurality of second energy windows is used on a side away from the FOV, wherein the first energy window is different from each of the plurality of second energy windows.

15. The PET system of claim 7, wherein a first energy window is used on a side close to a field of view (FOV) of the PET system, and a plurality of second energy windows is used on a side away from the FOV, wherein the first energy window is different from each of the plurality of second energy windows.

16. The electronic device of claim 8, wherein the method further comprises:

obtaining an upper limit and a lower limit of a target energy window based on a detector parameter of the detector, wherein the target energy window includes the first energy window and/or the second energy window, and the detector parameter includes at least one of:

an energy resolution of the detector in the plurality of detector layers, a material type of a scintillation crystal in the detector, a size of the scintillation crystal, or a resolution of a depth of interaction of the photons in the PET system.

17. The electronic device of claim 8, wherein the obtaining the upper limit and the lower limit of the target energy window based on the detector parameter of the detector includes:

determining an initial value of the upper limit and an initial value of the lower limit according to the detector parameter;

determining an initial energy window based on the initial value of the upper limit and the initial value of the lower limit;

determining a system parameter of the PET system based on the initial energy window, wherein the system parameter includes at least one of a sensitivity and a noise equivalent count metric;

updating the upper limit and the lower limit of the initial energy window based on the system parameter to obtain an updated initial energy window including an updated upper limit and an updated lower limit;

performing an iteration calculation on the system parameter based on the updated initial energy window; and in response to determining that the system parameter is within a preset threshold range, determining the updated upper limit and the updated lower limit as the upper limit and the lower limit of the target energy window, wherein the preset threshold range is determined based on the detector parameter.

18. The electronic device of claim 8, wherein the obtaining the absorption depth curve of the photons of the detector of the PET system, and dividing the detector into the first region and the second region along the depth direction of the detector based on the absorption depth curve includes:

determining a proportion of each type of a plurality of types of scattering events based on the absorption depth curve, wherein the plurality of types of the scattering events include the scattering events occurred in the scanning target and the scattering events occurred in the detector; and dividing the detector into the first region and the second region along the depth direction of the detector based on the proportion of the each type of scattering events.

19. The electronic device of claim 8, wherein after determining the plurality of second energy windows in the second region, the method further comprises:

obtaining a depth of interaction of the photons by the detector of the PET system; and determining a region and an energy window corresponding to the photons based on the depth of interaction of the photons, wherein the region is the first region or the second region, and the energy window is the first energy window corresponding to the first region or the second energy window corresponding to the second region.

20. The electronic device of claim 8, wherein each of the plurality of detector layers corresponds to the first energy window or the second energy window.

\* \* \* \* \*